United States Patent
Lackey et al.

(10) Patent No.: US 7,141,576 B2
(45) Date of Patent: Nov. 28, 2006

(54) CANCER TREATMENT METHOD

(75) Inventors: Karen Elizabeth Lackey, Durham, NC (US); Neil Spector, Chapel Hill, NC (US); Edgar Raymond Wood, III., Durham, NC (US); Wenle Xia, Durham, NC (US)

(73) Assignee: SmithKline Beecham (Cork) Limited, Carrigaline (IE)

( * ) Notice: Subject to any disclaimer, the term of this patent is extended or adjusted under 35 U.S.C. 154(b) by 55 days.

(21) Appl. No.: 10/466,290

(22) PCT Filed: Jan. 14, 2002

(86) PCT No.: PCT/US02/01130

§ 371 (c)(1), (2), (4) Date: Jul. 15, 2003

(87) PCT Pub. No.: WO02/056912

PCT Pub. Date: Jul. 25, 2002

(65) Prior Publication Data

US 2004/0053946 A1 Mar. 18, 2004

Related U.S. Application Data

(60) Provisional application No. 60/262,402, filed on Jan. 16, 2001.

(51) Int. Cl.
*A61K 31/517* (2006.01)
*A61P 35/00* (2006.01)

(52) U.S. Cl. ............... 514/264.11; 514/266.2; 514/266.24

(58) Field of Classification Search ......... 514/264.11, 514/266.2, 266.24
See application file for complete search history.

(56) References Cited

U.S. PATENT DOCUMENTS

| | | | |
|---|---|---|---|
| 6,169,091 B1 | 1/2001 | Cockerill et al. | |
| 6,174,889 B1 | 1/2001 | Cockerill et al. | |
| 6,207,669 B1 | 3/2001 | Cockerill et al. | |
| 6,262,107 B1 * | 7/2001 | Li et al. | 514/449 |
| 6,316,462 B1 * | 11/2001 | Bishop et al. | 514/290 |
| 6,391,874 B1 | 5/2002 | Cockerill et al. | |

FOREIGN PATENT DOCUMENTS

| | | |
|---|---|---|
| WO | 99/35146 | 7/1999 |
| WO | 01/04111 | 1/2001 |
| WO | 02/02552 | 1/2002 |

OTHER PUBLICATIONS

Goodman &Gilman's, The Pharmacological Basis of Therapeutics, Ninth Edition, (1996), Section X, Calabresi et al., pp. 1225-1230.*
Olson and Yun, "Anticancer Agents", Clinical Pharmacology Made Ridiculoulsy Simple, Edition 2, 1991, pp. 121-132.*
Goodman &Gilman's, The Pharmacological Basis of Therapeutics, Ninth Edition, (1996), Section X, Calabresi et al., pp. 1225-1232.*

* cited by examiner

*Primary Examiner*—Ardin H. Marschel
*Assistant Examiner*—C. Delacroix-Muirheid
(74) *Attorney, Agent, or Firm*—Kathryn L. Coulter; John L. Lemanowicz

(57) ABSTRACT

A method of treating cancer is described including administration of a 4-quinazolineamine and at least one other anti-neoplastic agent as well as pharmaceutical combinations and compositions containing the same.

2 Claims, 3 Drawing Sheets

CANCER TREATMENT METHOD

This application is filed pursuant to 35 U.S.C. § 371 as a U.S. National Phase Application of International Application No. PCT/US02/01130 filed Jan. 14, 2002, which claims priority from 60/262,402 filed Jan. 16, 2001.

BACKGROUND OF THE INVENTION

The present invention relates to pharmaceutical combinations and methods of treating cancer utilizing the same. Specifically, the invention relates to a combination of one of several quinazoline derivatives, which are inhibitors of erb-B2 and/or EGFR and other anti-neoplastics, as well as use of the combination in the treatment of cancer.

Effective treatment of hyperproliferative disorders, including cancer, is a continuing goal in the oncology field. Protein tyrosine kinases catalyse the phosphorylation of cell growth and differentiation of specific tyrosyl residues in various proteins involved in the regulation of cell growth and differentiation. (A. F. Wilks, Progress in Growth Factor Research, 1990, 2, 97–111; S. A. Courtneidge, Dev. Supp.1, 1993, 57–64; J. A. Cooper, Semin. Cell Biol., 1994, 5(6), 377–387; R. F. Paulson, Semin. Immunol., 1995, 7(4), 267–277; A. C. Chan, Curr. Opin. Immunol., 1996, 8(3), 394–401). Inappropriate or uncontrolled activation of many of such kinases, i.e., aberrant protein tyrosine kinase activity, for example by over-expression or mutation, has been shown to result in uncontrolled cell growth.

The erbB family of protein tyrosine kinases is one group of such kinases which has been implicated in human malignancies. Elevated EGFr activity has, for example, been implicated in non-small cell lung, bladder and head and neck cancers, and increased c-erbB-2 activity in breast, ovarian, gastric and pancreatic cancers. Consequently, inhibition of such protein tyrosine kinases should provide a treatment for disorders characterized by aberrant erb family protein kinase activity.

International Patent Application PCT/EP99/00048 filed Jan. 8, 1999, and published as WO 99/35146 on Jul. 15, 1999, discusses PTKs including erbB family PTKs. This published application discloses bicyclic heteroaromatic compounds, including N-{3-Chloro-4-[(3-fluorobenzyl)oxy]phenyl}-6-[5-({[2-(methanesulphonyl)ethyl]amino}methyl)-2-furyl]-4-quinazolinamine; (4-(3-Fluoro-benzyloxy)-3-chlorophenyl)-(6-(2-((2-methanesulphonyl-ethylamino)-methyl)-thiazol-4-yl)quinazolin-4-yl)-amine; (4-(3-Fluoro-benzyloxy)-3-bromophenyl)-(6-(5-((2-methanesulphonyl-ethylamino)-methyl)-furan-2-yl)quinazolin-4-yl)-amine as well as hydrochloride salts thereof. These compounds show inhibition activity against erbB family PTKs.

Combination therapy is rapidly becoming the norm in cancer treatment, rather than the exception. Oncologists are continually looking for anti-neoplastic compounds which when utilized in combination provides a more effective and/or enhanced treatment to the individual suffering the effects of cancer. Typically, successful combination therapy provides improved and even synergistic effect over monotherapy.

The present inventors have now identified combinations of chemotherapeutic agents that provide increased activity over monotherapy. In particular, multiple drug combinations that include inhibitors of the erbB family of kinases in combination with other anti-neoplastic agents.

SUMMARY OF THE INVENTION

In a first aspect of the present invention, there is provided a method of treating cancer in a mammal, including administering to said mammal a therapeutically effective amount of (a) a compound of formula I,

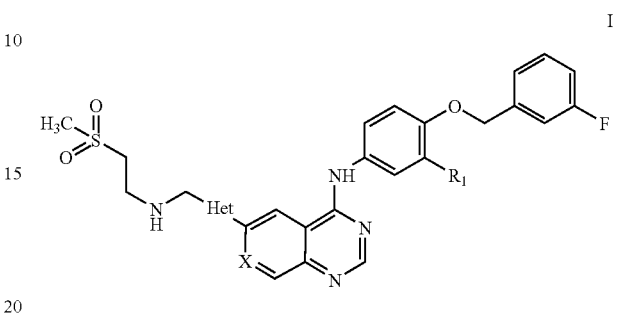

and salts, solvates or physiologically functional derivatives thereof,
wherein $R_1$ is Cl or Br; X is CH, N, or CF; and Het is thiazole or furan; and
(b) at least one anti-neoplastic agent.

In a second aspect of the present invention, there is provided a pharmaceutical combination including therapeutically effective amounts of: (a) a compound of formula I and salts, solvates or physiologically functional derivatives thereof and (b) at least one anti-neoplastic agent.

In a third aspect of the present invention, there is provided a pharmaceutical combination including a therapeutically effective amount of (a) a compound of formula I and salts, solvates or physiologically functional derivatives thereof and (b) at least one anti-neoplastic agent for use in therapy.

In a fourth aspect of the present invention, there is provided use of a pharmaceutical combination including therapeutically effective amounts of (a) a compound of formula I and salts, solvates or physiologically functional derivatives thereof and (b) at least one anti-neoplastic agent in the preparation of a medicament for use in the treatment of cancer.

DETAILED DESCRIPTION OF THE INVENTION

Figure 1:
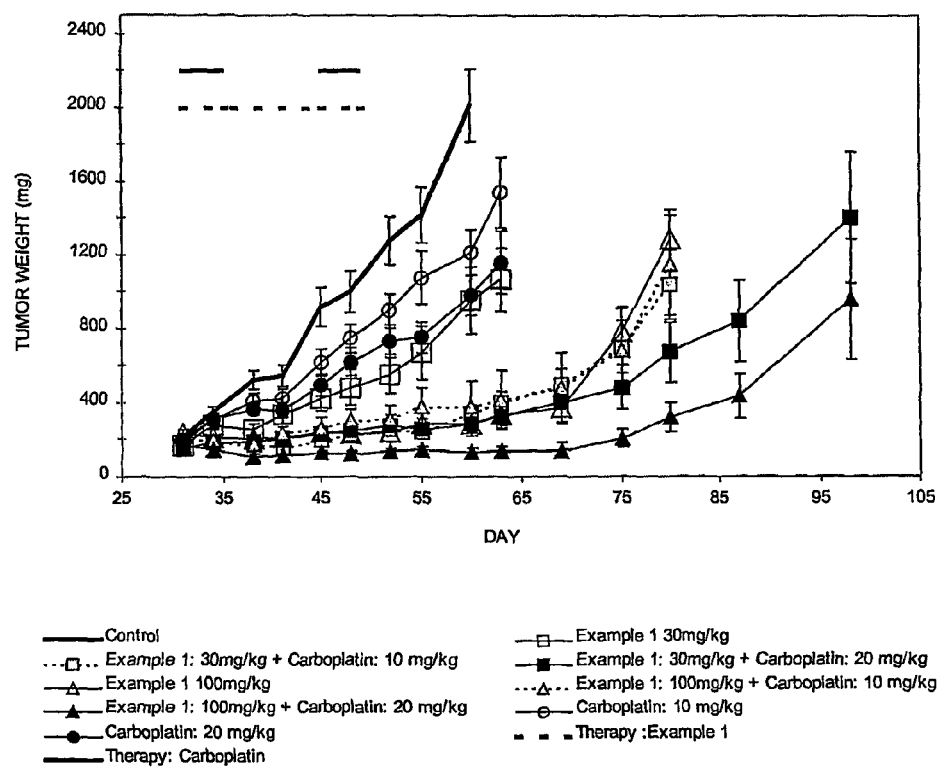
FIG. 1 depicts anti-tumor activity in a subcutaneous human xenograft mouse model dosed with a compound of Example 1 and carboplatin individually and in combination versus HN5 (human head and neck tumor line).

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "physiologically functional derivative" refers to any pharmaceutically acceptable derivative of a compound of Formulae I, II, III, or IV, for example, an ester or an amide, which upon administration to a mammal is capable of providing (directly or indirectly) a compound of Formulae I, II, III, or IV or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula I, II, III, or IV or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

The compounds of formulae I, II, III and IV have the ability to crystallize in more than one form, a characteristic, which is known as polymorphism, and it is understood that such polymorphic forms ("polymorphs") are within the scope of formulae I, II, III and IV. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Typically, the salts of the compounds of formula I, II, III, or IV are pharmaceutically acceptable salts. Salts encompassed within the term "pharmaceutically acceptable salts" refer to non-toxic salts of the compounds of this invention. Salts of the compounds of formula I, II, III, or IV may comprise acid addition salts derived from a nitrogen on a substituent in the compound of formula I, II, III, or IV. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate and ditosylate, triethiodide, trimethylammonium and valerate. Other salts, which are not pharmaceutically acceptable, may be useful in the preparation of compounds of this invention and these form a further aspect of the invention. Furthermore, such salt may be in anhydrous or hydrated form. In one embodiment, the compound of formula I, II, III, or IV is a hydrochloride or ditosylate salt, preferably a ditosylate salt, more preferably the monohydrate of the ditosylate salt.

The side chain $CH_3SO_2CH_2CH_2NHCH_2$ of the compounds of formula I, II, III, or IV may be linked to any suitable position of the group Het Similarly, the phenyl group of the quinazoline core may be linked to any suitable position of the group Het.

As recited above, a method of treating cancer is provided which includes administering therapeutically effective amounts of a compound of formula I and salts, solvates or physiologically functional derivatives thereof and at least one anti-neoplastic agent. The compound of formula I and salts, solvates or physiologically functional derivatives thereof are as defined above, that is $R_1$ is Cl or Br; X is CH, N, or CF; and Het is thiazole or furan.

It is to be understood that reference to compounds of formulae I above, and II, III, and IV following herein refers to compounds within the scope of these formulae as defined above unless specifically limited in subsequent reference to such formula with respect to $R_1$, Het, and X. It is also understood that the embodiments of the present invention described herein, including uses and compositions, are applicable to not only formula I, but to formula II, III, or IV, unless specifically stated otherwise.

In one embodiment, $R_1$ is Cl; X is CH; and Het is furan, preferably a compound of Formula II and salts, solvates or physiologically functional derivatives thereof.

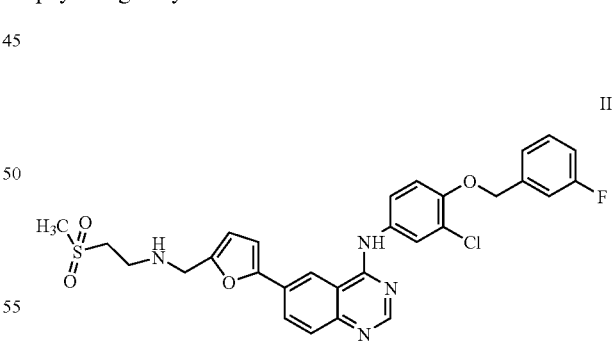

II

The compound of formula II has the chemical name N-{3-Chloro-4-[(3-fluorobenzyl)oxy]phenyl}-6-[5-({[2-(methanesulphonyl)ethyl]amino}methyl)-2-furyl]-4-quinazolinamine.

In another embodiment, $R_1$ is Cl; X is CH; and Het is thiazole, preferably a compound of formula III and salts, solvates or physiologically functional derivatives thereof.

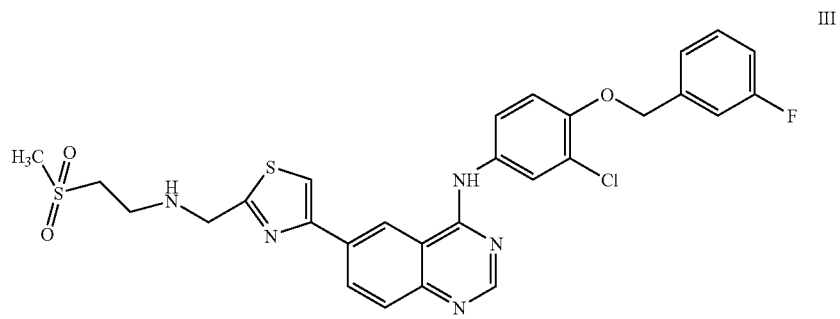

III

The compound of formula III is (4-(3-Fluoro-benzyloxy)-3-chlorophenyl)-(6-(2-((2-methanesulphonyl-ethylamino)-methyl)-thiazol-4-yl)quinazolin-4-yl)-amine.

In a further embodiment, $R_1$ is Br; X is CH; and Het is furan, preferably, a compound of formula IV and salts, solvates or physiologically functional derivatives thereof.

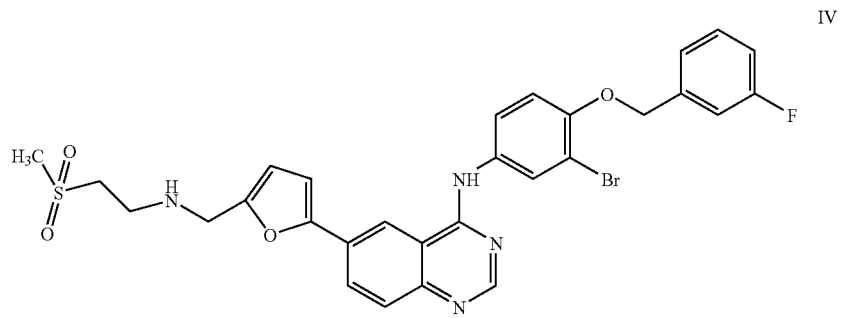

IV

The compound of formula IV is (4(3-Fluoro-benzyloxy)-3-bromophenyl)-(6-(5-((2-methanesulphonyl-ethylamino)-methyl)-furan-2-yl)quinazolin-4-yl)-amine.

Typically, any anti-neoplastic agent that has activity versus a susceptible tumor being treated may be utilized in the cancer treatment method of the present invention. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7,β10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561–1565 (1980); Schiff et al., Nature, 277:665–667 (1979); Kumar, J. Biol, Chem, 256: 10435–10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219–235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16–23, 1995).

Docetaxel, (2R,3S)-N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R-(R*,R*)-2,3-dihydroxybutanedioate(1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil,5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I—DNA complex. It is believed that cytotoxicity occurs as a result of irreparable double strand breaks caused by interaction of the topoisomerase I:DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I—DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

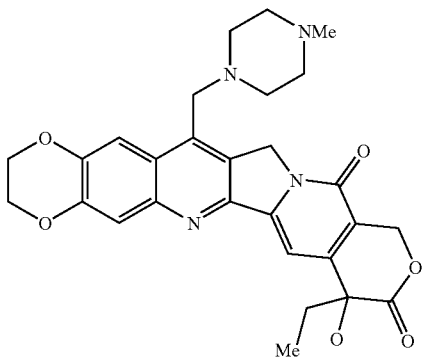

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor—I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803–818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465–80; and Bolen, J. B., Brugge, J. S., (1997) Annual review of Immunology. 15: 371–404.

SH2/SH3 domain blockers are agents that disrupt SH2 or SH3domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125–32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799–803; Brodt, P, Samani, A., and Navab, R. (2000), Biochemical Pharmacology, 60. 1101–1107; Massague, J., Weis-Garcia, F. (1996) Cancer Surveys. 27:41–64; Philip, P. A., and Harris, A. L. (1995), Cancer Treatment and Research. 78: 3–27, Lackey, K. et al Bioorganic and Medicinal Chemistry Letters, (10), 2000, 223–226; U.S. Pat. No. 6,268,391; and Martinez-Iacaci, L., et al, Int. J. Cancer (2000), 88(1), 44–52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412–8; Canman, C. E., Lim, D. S. (1998), Oncogene 17 (25) 3301–3308; Jackson, S. P. (1997), International Journal of Biochemistry and Cell Biology. 29 (7):935–8; and Zhong, H. et al, Cancer res, (2000) 60(6), 1541–1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292–8; Ashby, M. N. (1998), Current Opinion in Lipidology. 9 (2) 99–102; and BioChim. Biophys. Acta, (19899) 1423(3):19–30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269–286); Herceptin® erbB2 antibody (see Tyrosine Kinase Signalling in Breast cancer:erbB Family Receptor Tyrosine Kniases, Breast cancer Res., 2000, 2(3), 176–183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117–5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926–2935; Schreiber A B, Winkler M E, and Derynck R. (1986), Science, 232: 1250–1253; Yen L et al. (2000), Oncogene 19: 3460–3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569–3576; and Chen Y, Hu D, Eling D J, Robbins J, and Kipps T J. (1998), Cancer Res. 58: 1965–1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812–1823; and Kitada S et al. (1994), Antisense Res. Dev. 4: 71–79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215–230.

In one embodiment, the cancer treatment method of the claimed invention includes a compound of formula I and salts, solvates or physiologically functional derivatives thereof and at least one anti-neoplastic agent selected from the group consisting essentially of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

In another embodiment, the cancer treatment method of the claimed invention includes a compound of formula I and salts, solvates or physiologically functional derivatives thereof and at least one anti-neoplastic agent which is an anti-microtubule agent selected from diterpenoids and vinca alkaloids.

In a preferred embodiment, the cancer treatment method of the claimed invention includes a compound of formula I and salts, solvates or physiologically functional derivatives thereof and at least one anti-neoplastic agent, which is a diterpenoid.

In an alternative preferred embodiment, the cancer treatment method of the claimed invention includes a compound of formula I and salts, solvates or physiologically functional derivatives thereof and at least one anti-neoplastic agent, which is a vinca alkaloid.

In another preferred embodiment, the cancer treatment method of the claimed invention includes a compound of formula I and salts, solvates or physiologically functional derivatives thereof and at least one anti-neoplastic agent, which is a platinum coordination complex.

In a more preferred embodiment, the cancer treatment method of the claimed invention includes a compound of formula I and salts, solvates or physiologically functional derivatives thereof and at least one anti-neoplastic agent which is selected from the group consisting of paclitaxel, carboplatin, or vinorelbine.

In a more preferred embodiment, the cancer treatment method of the claimed invention includes a compound of formula I and salts, solvates or physiologically functional derivatives thereof and at least one anti-neoplastic agent, which is carboplatin.

In a more preferred embodiment, the cancer treatment method of the claimed invention includes a compound of formula I and salts, solvates or physiologically functional derivatives thereof and at least one anti-neoplastic agent, which is vinorelbine.

In a most preferred embodiment, the cancer treatment method of the claimed invention includes a compound of formula I and salts, solvates or physiologically functional derivatives thereof and at least one anti-neoplastic agent, which is paclitaxel.

In one embodiment, the cancer treatment method of the claimed invention includes a compound of formula II and salts, solvates or physiologically functional derivatives thereof and at least one anti-neoplastic agent selected from the group consisting essentially of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

In another embodiment, the cancer treatment method of the claimed invention includes a compound of formula II and salts, solvates or physiologically functional derivatives thereof and at least one anti-neoplastic agent which is an anti-microtubule agent selected from diterpenoids and vinca alkaloids.

In a preferred embodiment, the cancer treatment method of the claimed invention includes a compound of formula II and salts, solvates or physiologically functional derivatives thereof and at least one anti-neoplastic agent, which is a diterpenoid.

In an alternative preferred embodiment, the cancer treatment method of the claimed invention includes a compound of formula II and salts, solvates or physiologically functional derivatives thereof and at least one anti-neoplastic agent, which is a vinca alkaloid.

In another preferred embodiment, the cancer treatment method of the claimed invention includes a compound of formula II and salts, solvates or physiologically functional derivatives thereof and at least one anti-neoplastic agent, which is a platinum coordination complex.

In a more preferred embodiment, the cancer treatment method of the claimed invention includes a compound of formula II and salts, solvates or physiologically functional derivatives thereof and at least one anti-neoplastic agent which is selected from the group consisting of paclitaxel, carboplatin, or vinorelbine.

In a more preferred embodiment, the cancer treatment method of the claimed invention includes a compound of formula II and salts, solvates or physiologically functional derivatives thereof and at least one anti-neoplastic agent, which is carboplatin.

In a more preferred embodiment, the cancer treatment method of the claimed invention includes a compound of formula II and salts, solvates or physiologically functional derivatives thereof and at least one anti-neoplastic agent, which is vinorelbine.

In a most preferred embodiment, the cancer treatment method of the claimed invention includes a compound of formula II and salts, solvates or physiologically functional derivatives thereof and at least one anti-neoplastic agent, which is paclitaxel.

In one embodiment, the cancer treatment method of the claimed invention includes a compound of formula III and salts, solvates or physiologically functional derivatives thereof and at least one anti-neoplastic agent selected from the group consisting essentially of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

In another embodiment, the cancer treatment method of the claimed invention includes a compound of formula III and salts, solvates or physiologically functional derivatives thereof and at least one anti-neoplastic agent which is an anti-microtubule agent selected from diterpenoids and vinca alkaloids.

In a preferred embodiment, the cancer treatment method of the claimed invention includes a compound of formula III and salts, solvates or physiologically functional derivatives thereof and at least one anti-neoplastic agent, which is a diterpenoid.

In an alternative preferred embodiment, the cancer treatment method of the claimed invention includes a compound of formula III and salts, solvates or physiologically functional derivatives thereof and at least one anti-neoplastic agent, which is a vinca alkaloid.

In another preferred embodiment, the cancer treatment method of the claimed invention includes a compound of formula III and salts, solvates or physiologically functional derivatives thereof and at least one anti-neoplastic agent, which is a platinum coordination complex.

In a more preferred embodiment, the cancer treatment method of the claimed invention includes a compound of formula III and salts, solvates or physiologically functional derivatives thereof and at least one anti-neoplastic agent which is selected from the group consisting of paclitaxel, carboplatin, or vinorelbine.

In a more preferred embodiment, the cancer treatment method of the claimed invention includes a compound of formula III and salts, solvates or physiologically functional derivatives thereof and at least one anti-neoplastic agent, which is carboplatin.

In a more preferred embodiment, the cancer treatment method of the claimed invention includes a compound of formula III and salts, solvates or physiologically functional derivatives thereof and at least one anti-neoplastic agent, which is vinorelbine.

In a most preferred embodiment, the cancer treatment method of the claimed invention includes a compound of formula III and salts, solvates or physiologically functional derivatives thereof and at least one anti-neoplastic agent, which is paclitaxel.

In one embodiment, the cancer treatment method of the claimed invention includes a compound of formula IV and salts, solvates or physiologically functional derivatives thereof and at least one anti-neoplastic agent selected from the group consisting essentially of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

In another embodiment, the cancer treatment method of the claimed invention includes a compound of formula IV and salts, solvates or physiologically functional derivatives thereof and at least one anti-neoplastic agent which is an anti-microtubule agent selected from diterpenoids and vinca alkaloids.

In a preferred embodiment, the cancer treatment method of the claimed invention includes a compound of formula IV and salts, solvates or physiologically functional derivatives thereof and at least one anti-neoplastic agent, which is a diterpenoid.

In an alternative preferred embodiment, the cancer treatment method of the claimed invention includes a compound of formula IV and salts, solvates or physiologically functional derivatives thereof and at least one anti-neoplastic agent, which is a vinca alkaloid.

In another preferred embodiment, the cancer treatment method of the claimed invention includes a compound of formula IV and salts, solvates or physiologically functional derivatives thereof and at least one anti-neoplastic agent, which is a platinum coordination complex.

In a more preferred embodiment, the cancer treatment method of the claimed invention includes a compound of formula IV and salts, solvates or physiologically functional derivatives thereof and at least one anti-neoplastic agent which is selected from the group consisting of paclitaxel, carboplatin, or vinorelbine.

In a more preferred embodiment, the cancer treatment method of the claimed invention includes a compound of formula IV and salts, solvates or physiologically functional derivatives thereof and at least one anti-neoplastic agent, which is carboplatin.

In a more preferred embodiment, the cancer treatment method of the claimed invention includes a compound of formula IV and salts, solvates or physiologically functional derivatives thereof and at least one anti-neoplastic agent, which is vinorelbine.

In a most preferred embodiment, the cancer treatment method of the claimed invention includes a compound of formula IV and salts, solvates or physiologically functional derivatives thereof and at least one anti-neoplastic agent, which is paclitaxel.

The compounds of the Formula I, including compounds of formulae II, III, and IV, or salts, solvates, or physiologically functional derivatives thereof and the at least one anti-neoplastic agent may be employed in combination concomitantly or sequentially in any therapeutically appropriate combination. The combination may be employed in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one is administered first and the other second or vice versa. Such sequential administration may be close in time or remote in time.

The cancer treatment method of the present invention may also include administration of at least one additional cancer treatment therapy in combination concomitantly or sequentially in any therapeutically appropriate combination with the combinations of the present invention. The additional cancer treatment therapy may include radiation therapy, surgical therapy and/or at least one additional chemotherapeutic therapy including administration of at least one additional anti-neoplastic agent.

As recited above, a pharmaceutical combination including compounds of the Formula I, including compounds of formulae II, III, IV, or salts, solvates, or physiologically functional derivatives thereof and the at least one anti-neoplastic agent is provided for in the present invention. Such compounds of formulae I, II, III, and IV and the at least one anti-neoplastic agent are as described above and may be utilized in any of the combinations described above in the method of treating cancer of the present invention.

While it is possible that, for use in therapy, therapeutically effective amounts of compounds of formula I, II, III, IV as well as salts, solvates and physiologically function derivatives thereof and the at least one anti-neoplastic agent, may be administered as the raw chemical, it is possible to present the active ingredient as a pharmaceutical composition. As indicated above, such elements of the pharmaceutical combination utilized may be presented in separate pharmaceutical compositions or formulated together in one pharmaceutical formulation. Accordingly, the invention further provides a combination of pharmaceutical compositions one of which includes therapeutically effective amounts of compounds of the formula I and salts, solvates, and physiologically functional derivatives thereof, and one or more pharmaceutically acceptable carriers, diluents, or excipients and a pharmaceutical composition containing at least one anti-neoplastic agent and one or more pharmaceutically acceptable carriers, diluents, or excipients.

Alternatively, a pharmaceutical composition is provided which includes therapeutically effective amounts of a compound of the formula I and salts, solvates, and physiologically functional derivatives thereof, at least one anti-neoplastic agent and one or more pharmaceutically acceptable carriers, diluents, or excipients. The compounds of the formula I, including compounds of formulae II, III, and IV, and salts, solvates, and physiologically functional derivatives thereof, and the at least one anti-neoplastic agent are as described above and may be utilized in any of the combinations described above in the method of treating cancer of the present invention.

The carrier(s), diluent(s) or excipient(s) must be acceptable in the sense of being compatible with the other ingredients of the formulation and not deleterious to the recipient thereof. According to another aspect of the invention there is also provided a process for the preparation of a pharmaceutical formulation including admixing a compound of the formula I, or salts, solvates, or physiologically functional derivatives thereof, and/or at least one anti-neoplastic agent with one or more pharmaceutically acceptable carriers, diluents or excipients.

The components of the pharmaceutical compositions, of the present invention, may be formulated for administration by any route, and the appropriate route will depend on the specific cancer being treated as well as the subjects to be treated. Suitable pharmaceutical formulations include those for oral, rectal, nasal, topical (including buccal, sub-lingual, and transdermal), vaginal or parenteral (including intramuscular, sub-cutaneous, intravenous, and directly into the affected tissue) administration or in a form suitable for administration by inhalation or insufflation. The formulations may, where appropriate, be conveniently presented in discrete dosage units and may be prepared by any of the methods well know in the pharmacy art.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methylcellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The components of the pharmaceutical compositions of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The components of the pharmaceutical compositions of the present invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouthwashes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of the components of the pharmaceutical compositions of the present invention will depend on a number of factors including, but not limited to, the age and weight of the mammal, the precise disorder requiring treatment and its severity, the nature of the formulation, and the route of administration, and will ultimately be at the discretion of the attendant physcian or veternarian. Typically, the components of the pharmaceutical compositions of the present invention will be given for treatment in the range of 0.1 to 100 mg/kg body weight of recipient (mammal) per day and more usually in the range of 1 to 10 mg/kg body weight per day. Acceptable daily dosages, may be from about 0.1 to about 1000 mg/day, and preferably from about 0.1 to about 100 mg/day.

The pharmaceutical combinations and compositions, including compounds of formula I and salts, solvates, and physiologically functional derivatives thereof and at least one anti-neoplastic agent, described above, are useful in therapy and in the preparation of medicaments for treating cancer in a mammal.

In one embodiment, the mammal in the methods and uses of the present invention is a human.

The following examples are intended for illustration only and are not intended to limit the scope of the invention in any way. The physical data given for the compounds exemplified is consistent with the assigned structure of those compounds.

EXAMPLES $^1$H NMR spectra were obtained at 500 MHz on a Bruker AMX500 spectrophotometer, on a Bruker spectrophotometer at 300 MHz, on a Bruker AC250 or Bruker AM250 spectrophotometer at 250 MHz and on a Varian Unity Plus NMR spectrophotometer at 300 or 400 MHz. J values are given in Hz. Mass spectra were obtained on one of the following machines: VG Micromass Platform (electrospray positive or negative), HP5989A Engine (thermospray positive) or Finnigan-MAT LCQ (ion trap) mass spectrometer. Analytical thin layer chromatography (tlc) was used to verify the purity of some intermediates which could not be isolated or which were too unstable for full characterization, and to follow the progress of reactions. Unless otherwise stated, this was done using silica gel (Merck Silica Gel 60 F254).

The free base, HCl salts, and ditosylate salts of the compounds of formulae (I), (II), (III), and (IV), may be prepared according to the procedures of the International Patent Application No. PCT/EP99/00048, filed Jan. 8, 1999, and published as WO 99/35146 on Jul. 15, 1999 and of co-pending U.S. Provisional application No. 60/215,508 filed Jun. 30, 2000. Such applications are incorporated herein by reference to the extent they teach the preparation of the compounds of formula (I), (II), (III), and (IV) and salts thereof. Some of such procedures are recited again herein as well as additional variations and procedures.

General Procedures (A) Reaction of an Amine with a Bicyclic Species Containing a 4-chloropyrimidine or 4-chloropyridine Ring The optionally substituted bicyclic species and the specified amine were mixed in an appropriate solvent (typically acetonitrile unless otherwise specified, although ethanol, 2-propanol or DMSO may also be used), and heated to reflux. When the reaction was complete (as judged by tlc), the reaction mixture was allowed to cool. The resulting suspension was diluted, e.g. with acetone, and the solid collected by filtration, washing e.g. with excess acetone, and dried at 60° C. in vacuo, giving the product as the hydrochloride salt. If the free base was required (e.g. for further reaction), this was obtained by treatment with a base e.g. triethylamine; purification by chromatography was then performed if required.

(B) Reaction of a Product from Procedure (A) with a Heteroaryl Tin Reagent

A stirred mixture of the product from (A), (containing a suitable leaving group such as chloro, bromo, iodo or triflate), a heteroaryl stannane and a suitable palladium catalyst, such as bis(triphenylphosphine)palladium (II) chloride or 1,4-bis(diphenylphosphino)butane palladium (II) chloride (prepared as described in C. E. Housecroft et. al., Inorg. Chem., (1991), 30(1), 125–130), together with other appropriate additives (such as diisopropylethylamine or lithium chloride), were heated at reflux in dry dioxane or another suitable solvent (e.g. DMF) under nitrogen until the reaction was complete. The resulting mixture was generally purified by chromatography on silica.

(C) Removal of a 1,3-dioxolan-2-yl Protecting Group to Liberate an Aldehyde

The compound containing the 1,3-dioxolan-2-yl group was suspended in an appropriate solvent, e.g., THF and treated with hydrochloric acid, either as an aqueous solution (e.g. 2N) or as a solution in dioxane (e.g. 4 molar) and stirred at ambient temperature until the reaction was judged complete (e.g. by tlc or LC/MS analysis). Generally the mixture was diluted with water, and the resulting precipitate was collected by filtration, washed with water and dried to give the aldehyde.

(D) Reaction of an Aldehyde with an Amine by Reductive Amination

An aldehyde (such as the product of C) and the required primary or secondary amine were stirred together in a suitable solvent (such as dichloromethane) containing glacial acetic acid (4A molecular sieves may also be present) for ca. 1 h. A suitable reducing agent, such as sodium (triacetoxy) borohydride was then added and stirring continued under nitrogen until the reaction was complete (as judged by hplc or tlc). The resulting mixture was washed with an aqueous basic solution (e.g. sodium or potassium carbonate) and extracted with a suitable solvent, e.g. dichloromethane. The dried organic phase was evaporated and the residue purified either by column chromatography or by Bond Elut™ cartridge. If desired, the isolated material was then converted into the hydrochloride salt e.g. by treatment with ethereal hydrogen chloride.

Example 1

Preparation of N-{3-Chloro-4-[(3-fluorobenzyl)oxy]phenyl}-6-[5-({[2-(methylsulfonyl)ethyl]amino}methyl)-2-furyl]-4-quinazolinamine and di-hydrochloride and ditosylate salts thereof

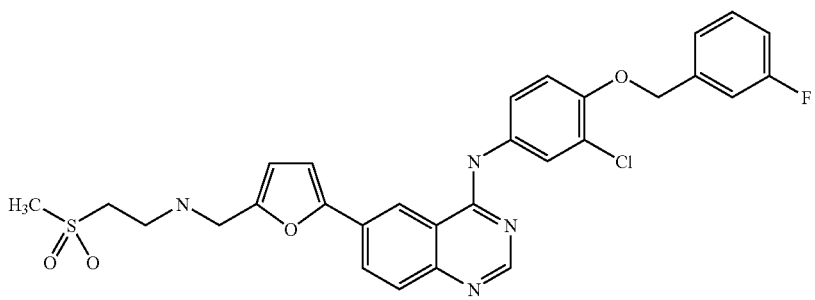

(a) Preparation of 4-Hydroxy-7-iodoquinazoline

5-Iodoanthranilic acid (25 g) and formamide (200 mL) was combined and warmed to 190° C. for 2 hours. After 15 minutes the reaction appeared to completely dissolve. The reaction was cooled down to room temperature, poured into water (500 mL) and allowed to stand for 1–2 hours. The desired product was collected by filtration.

(b) Preparation of 4-Chloro-7-iodoquinazoline

7-Iodoquinazolin-4-one (0.46 g) was treated with phosphorous oxychloride (5 ml) at reflux under nitrogen for 2 hours. The mixture was cooled, evaporated and partitioned between saturated aqueous sodium carbonate and ethyl acetate. The organic phase was dried and concentrated in vacuo to give the title compound (0.43 g); m/z (M+1+) 291.

(c) 4-(3-fluorobenzyloxy)-3-chloro nitrobenzene 2-chloro-4-nitrophenol (9.02 g, 52 mmol)), 3-fluorobenzyl bromide (9.85 g, 52 mmol) and acetonitrile (90 mL) was combined at room temperature under nitrogen. Potassium carbonate (7.9 g, 57 mmol)) was added and the reaction mixture stirred at 60° C. for 2 hours and then cooled to room temperature. After cooling the reaction mixture was poured into water. The solids were collected by filtration and washed with diethyl ether to afford the desired product (13.98 g, 95% yield). [TLC system=1:1 EtOAc:Hexanes, $R_f$=0.76]

(d) Preparation of 4-(3-fluorobenzyloxy)-3-chloro aniline

Under nitrogen, a Parr Shaker flask was charged with Pt/C 5% (135 mg) and ethanol (180 mL) and 4-(3-fluorobenzyloxy)-3-chloro nitrobenzene (13.5 g) was added. The reaction vessel was placed on a Parr Shaker Apparatus under 25 psi of $H_2$ for 50 minutes. The catalyst was then removed by filtration through Celite and the filtrate concentrated to afford a light grey solid. The filtrate was triturated with diethyl ether and the solids collected by filtration (12.05 g, ~100% yield).

(e) 6-Iodo-(4-(3-fluorobenzyloxy)-3-chlorophenyl)-quinazolin-4-yl)amine 4-(3-fluorobenzyloxy)-3-chlorophenyl)-amine (12.3 g, 49 mmol), 4-chloro-6-iodoquinazoline 14.2 g, 49 mmol) and isopropanol (250 mL) were combined and the reaction mixture was heated to 70° C. for 3.5 hours. The resultant bright yellow solid product was collected by filtration (25.5 g, 96/% yield). $^1$H NMR (DMSO-d6) δ 9.83 (s, 1H); 8.92 (s, 1H); 8.58 (s, 1H); 8.09 (d, 1H); 8.00 (d, 1H); 7.61 (d, 1H); 7.52 (d, 1H); 7.44 (m, 1H); 7.20–7.33 (m, 3H); 7.15 (m, 1H); 5.21 (s, 2H); MS m/z 506 (M+1)

(f) Preparation of 5-(4-{3-chloro-4-(3-fluorobenzyloxy)-anilino}-6-quinazolinyl)-furan-2-carbaldehyde The title compound was prepared according to Procedure B followed by Procedure C from 6-Iodo-(4-(3-fluorobenzyloxy)-3-chlorophenyl)-quinazolin-4-yl)amine (1.0 g, 1.82 mmol) and (1,3 dioxolan-2-yl)-2-(tributylstannyl)furan (11.17 g, 2.73 mmol). $^1$H NMR 400 MHz (DMSO-d6) δ12.05 (s, 1H); 9.68 (s, 1H); 9.43 (s, 1H); 8.95 (s, 1H); 8.53 (d, 1H); 7.99 (D, 1H); 7.92 (s, 1H); 7.78 (m, 1H); 7.66 (m, 1H); 7.63 (m, 1H); 7.47 (m, 1H); 7.40–7.30 (M, 3H); 7.19 (m, 1H); 5.31 (s, 2H); MS m/z 472 (M+H).

(g) Preparation of N-{3-Chloro-4-[(3-fluorobenzyl)oxy]phenyl}-6-[5-({[2-(methylsulfonyl)ethyl]amino}methyl)-2-furyl]-4-quinazolinamine The title compound was prepared according to Procedure D as follows. The 5-(4-{3-chloro-4-(3-fluorobenzyloxy)-anilino}-6-quinazolinyl)-furan-2-carbaldehyde (12.58 g, 24.7 mmol) was added to a solution of 2-methanesulphonyl-ethylamine (4.55 g, 37.0 mmol) and triethylamine(2.0 ml, 27.2 mmol) in 125 ml of tetrahydrofuran and 125 ml of methanol. After stirring 3 hours, the solution was cooled in an ice bath and sodium borohydride(2.42 g, 64.0 mmol) was added in five portions over a 20 minute period. The reaction mixture was stirred overnight at room temperature and then quenched with the dropwise addition of 250 ml of water. The solution was concentrated in vacuo to remove the organic solvents and the residual oily solution was extracted with 1 l of ethyl acetate. The organic solution was washed with 1M sodium hydroxide and brine and then dried with sodium sulfate. The solution was concentrated in vacuo to a very small volume and solid crystallized out. The suspension was filtered with a small volume of ethyl acetate, washed with ether and dried in a vacuum oven at 65 C to give 10.0 g(70%) of free base as an off white solid. $^1$H NMR 400 MHz (DMSO-d6) δ 9.60 (bs, 1H); 9.32 (bs, 1H); 8.82 (bs, 1H); 8.34 (d, 1H); 8.0 (s, 1H); 7.88 (d, 1H); 7.74 (d 1H); 7.45 (m, 1H); 7.34-7.23 (m, 4H); 7.17 (m, 1H); 6.83 (d, 1H); 5.27 (s, 2H); 4.42 (s, 2H); 3.59 (m, 2H); 3.40 (m, 2H, obscured by waterpeak); 3.12 (s, 3H); MS m/581 (M+H$^+$).

(h) Preparation of 5-(4-[3-chloro-4-(3-fluorobenzyloxy)-anilino]-6-quinazolinyl)-furan-2-carbaldehyde tosylate A 2 liter, 3 neck round bottom flask equipped with a mechanical stirrer was charged with 74.95 grams of the HCl salt of 5-(4-[3-chloro-4-(3-fluorobenzyloxy)-anilino]-6-quinazolinyl)-furan-2-carbaldehyde (prepared according to the Procedure D and Examples 1 (a)–(g), and 749.5 mL THF. To this slurry was charged 84.45 mL of 2M NaOH and the reactants were stirred for 30 minutes. The layers were separated and then the organic layer was washed with 160 mL of $H_2O$. The organic layer was slurried with 3.75 grams of Darco G60 and filtered through celite. The filtrate was collected and slowly added to 33.54 grams of toluene-sulfonic acid monohydrate with rapid stirring. The solids slowly precipitated out at ambient temperature. The mixture was cooled to 0° C. and stirred for 10 minutes. The mixture was filtered and pulled dry with a rubber dam, then dried in vacuo at 50° C. overnight. The yield of 5-(4-[3-chloro-4-(3-fluorobenzyloxy)-anilino]-6-quinazolinyl)-furan-2-carbaldehyde tosylate was 84.25 grams (88.8%).

(i) Preparation of N-{3-Chloro-4-[(3-fluorobenzyl)oxy]phenyl}-6-[5-({[2-(methanesulphonyl)ethyl]amino}methyl)-2-furyl]-4-quinazolinamine ditosylate anhydrate To a 20 L reactor was added 13.3 vol of THF followed by 0.62 wt (2.93 mol) of NaBH(OAc)$_3$. The 20 L reactor was set to maintain contents at 20° C. A second 20 L reactor was charged with 1000 grams, (1.55 mol) of 5-(4-[3-chloro-4-(3-fluorobenzyloxy)-anilino]-6-quinazolinyl)-furan-2-carbaldehyde tosylate prepared by the procedure of Example 1 and 6.7 vol of THF. To the THF solution of 5-(4-[3-chloro-4-(3-fluorobenzyloxy)-anilino]-6-quinazolinyl)-furan-2-carbaldehyde tosylate was added 0.325 vol (1.86 mol) diisopropylethylamine followed by 0.32 wt of 2-(methylsulfone)ethylamine, (321 g, 2.6 mol) and 0.15 vol of IPA. After 1 hour, the preformed imine/THF solution was transferred by vacuum to the stirred suspension of NaBH(OAc)$_3$ in the first 20 L reactor over 10 minutes. After 90 minutes, 4 vol of 5N NaOH was added over 40 minutes via a pump. This solution was allowed to stir for 15 minutes after which the stirrer was switched off and the layers were allowed to separate. The aqueous layer was drained from the bottom of the reactor and the organic layer transferred to the empty 20 L reactor through a teflon-lined stainless steel jacketed transfer hose outfitted with an in-line 0.45 µm filter. To this solution was added a 2 vol THF solution of 4 wt (1180 g, 6.2 mole) of p-toluenesulfonic acid monohydrate over 5 minutes. A yellowish precipitate was observed to come out of solution and this was allowed to stir at room temperature for 12 hours. The reaction was drained from the bottom of the reactor and filtered through a ceramic filter lined with paper. The yellow filter cake was washed with 1 vol of a 95:5 THF/water solution and allowed to air dry overnight. After suctioning dry for 12 hours, the yellow filter cake was transferred to two glass trays and placed in the drying oven (42° C.) under house vacuum (18 in Hg) with a nitrogen bleed. The two glass trays were removed from the oven and allowed to cool to room temperature and sampled accordingly. The isolated yield of N-{3-Chloro-4[(3-fluorobenzyl)oxy]phenyl}-6-[5-({[2-(methane-sulphonyl)ethyl]amino}methyl)-2-furyl]-4-quinazolinamine ditosylate (anhydrate) was 1264 grams (1.3 wt, 88%; 1443 g Th) and was a yellow solid.

Approximately 50 mg of the product was transferred to a Karl Fisher Volumetric Moisture Apparatus (model DL35, Mettler, Hightstown, N.J.), which was operated according to the manufacturer's instructions. The anhydrate water content was determined to be 0.31%.

(j) Preparation of N-{3-Chloro-4-[(3-fluorobenzyl)oxy]phenyl}-6-[5-({[2-(methanesulphonyl)ethyl]amino}methyl)-2-furyl]-4-quinazolinamine ditosylate monohydrate (monohydrate form of compound of formula II)

A 20 L reactor was charged with 1 wt (930 g, 1.0 mol) of N-{3-Chloro-4-[(3-fluorobenzyl)oxy]phenyl}-6-[5-({[2-(methanesulphonyl)ethyl]amino}methyl)-2-furyl]-4-quinazolinamine ditosylate anhydrate prepared using the procedure of Example 2. To this was added 10 volumes of a pre-mixed 8:2 THF:deionized water solution and the reactor was heated to 65° C. Complete dissolution was observed at 50° C. The clear reaction mixture was transferred to another 20 L reactor through a stainless steel jacketed transfer hose that was equipped with an in-line 5.0 µm cartridge filter. The empty 20 L reactor and the filter line were washed with 0.2 vol of the pre-mixed 8:2 THF:deionized water solution. An additional 1 vol of pre-mixed 8:2 THF:deionized water solution was used to wash the material into the reaction mixture. The 20 L reactor was heated to ~80° C. The reaction temperature was then ramped down to 55° C. over 2 hours and then to 45° C. over 10 hours. After 10 hours, the temperature was adjusted to 25° C. and the reaction mixture allowed to stir at room temperature for 45 minutes. The yellow precipitate was drained from the bottom of the 20 L reactor into a ceramic filter lined with paper. The flow was fast and smooth and the filter rate very good. The yellow filter cake was washed with 0.6 volumes of a pre-mixed 8:2 THF:deionized water solution and the yellow solid was air dried for 4 hours and placed into a glass tray. The glass tray was placed in a vacuum oven under house vacuum (~18 in Hg) at 60° C. with a nitrogen bleed for 2 days. After removal from the oven, the material was sampled accordingly. The yield was 743 grams (0.8 wt, 80% o; 930 g th) as a bright yellow, crystalline solid.

Approximately 50 mg of the product was transferred to a Karl Fisher Volumetric Moisture Apparatus (model DL35, Mettler, Hightstown, N.J.), which was operated according to the manufacturer's instructions. The monohydrate water content was determined to be 1.99%, which is in agreement with the theoretical value of 1.92%.

Example 2

Preparation of (4-(3-Fluoro-benzyloxy-3-bromophenyl)-(6-(5-((2-methanesulphonyl-ethylamino)-methyl)-furan-2-yl)-quinazolin-4-yl)-amine and di-hydrochloride and ditosylate salts thereof (a) Preparation of 2-Bromo-4-nitrophenol 2-Bromo-4-nitroanisole (20 g, 0.086 mol) was dissolved in DMF (414 mL) at room temperature under $N_2$. Sodium ethylthiolate (17.4 g, 0.207 mol) was added and the reaction mixture was warmed to 115° C. for 2 hours. The reaction was cooled to room temperature and diluted with EtOAc (200 mL) and 1 M HCl (aq., 200 mL). The phases were separated, and the desired product was extracted into 1 M NaOH (aq, 150 mL×3). The basic aqueous extracts were combined and acidified using conc. HCl. The desired product was extracted from the acidic aqueous solution using EtOAc (250 mL×2). The combined organic layers were washed with brine and dried over sodium sulfate. The volatiles were removed in vacuo to afford a light brown semi-solid (9.8 g, 52% yield). $^1$H NMR (DMSO-d6) δ 8.33 (m, 1H); 8.09 (m, 1H); 7.07 (d, 1H).

(b) Preparation of 2-Bromo-1-(3-fluorobenzyloxy)-4-nitrobenzene

2-Bromo-4-nitrophenol (4.86 g, 0.0223 mol), triphenylphosphine (7.6 g, 0.0290 mol), 3-fluorobenzylalcohol (3.65 g, 0.0290 mol) were combined and dissolved in THF (89 mL). The reaction temperature was cooled to 0° C. and DIAD (4.50 g. 0.0290 mol) was added. The reaction was allowed to warm slowly to room temperature and stirred for 3 hours before it was diluted with water (1.00 mL) and EtOAc (100 mL). The layers were separated and the aqueous layer was extracted with EtOAc (200 mL×2). The organic extracts were combined and washed with brine, followed by drying over sodium sulfate. The volatiles were removed in vacuo and the residual semi-solid was treated with diethyl ether. The solids were removed by filtration. The volatiles from the resulting filtrate were removed in vacuo and the material was purified using EtOAc:Hexanes (90/10) in a biotage LC system to afford the title compound as a yellow solid (3.73 g. 68% yield). $^1$H NMR (DMSO-d6) δ 8.43 (d, 1H); 8.26 (m, 1H); 7.45 (m, 1H); 7.38 (d, 1H); 7.30 (m, 2H); 7.17 (m, 1H); 5.39 (s, 2H).

(c) Preparation of 3-Bromo-4-(3-fluorobenzyloxy)-aniline

Under a blanket of $N_2$, Pt/C (5%, 0.37 g) was charged to a Parr Shaker Flask. Ethanol (150 mL) and 2-bromo-1-(3-fluorobenzyloxy)-4-nitrobenzene (3.73 g, 0.011 mol) were added and the reaction mixture was placed on a Parr Shaker Apparatus under 30 psi of $H_2$ for 5 h. The reaction was filtered through a pad of elite to remove the catalyst and the volatiles were removed from the filtrate. The residue was dissolved in the $CH_2Cl_2$ (5 mL) and treated with conc. HCl (1 mL). The precipitate was collected by filtration and free-based using saturated aqueous sodium bicarbonate (2.27 g, 67% yield) $^1$H NMR (DMSO-d6) δ 7.4 (m, 1H); 7.23 (m, 2H); 7.11 (m, 1H); 6.86 (d, 1H); 6.77 (m, 1H); 6.48 (m, 1H); 5.0 (s, 2H); 4.93 (bs, 2H).

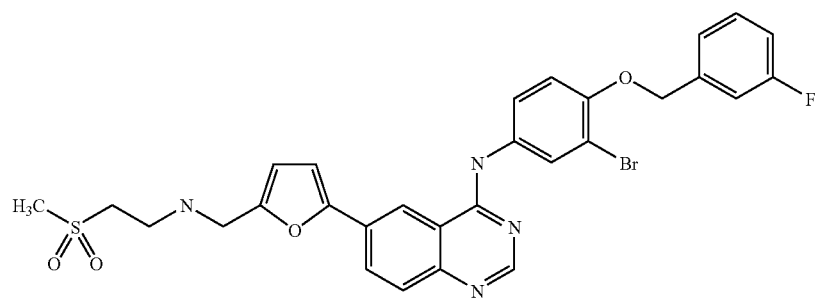

(d) Preparation of 6-Iodo-(4-(3-fluorobenzyloxy)-3-bromophenyl)-quinazolin-4-yl)amine The title compound was prepared according to Procedure A from 3-bromo-4-(3-fluorobenzyloxy)-aniline (0.79 g, 2.7 mmol) and 4-chloro-6-iodo-quinazoline (0.8 g, 2.7 mmol). $^1$H NMR (DMSO-d6) δ 11.1 (bs, 1H); 9.10 (s, 1H); 8.87 (s, 1H); 8.29 (d, 1H); 8.03 (s, 1H); 7.68 (m, 1H); 7.62 (d, 1H); 7.45 (m, 1H); 7.33–7.26 (m, 3H); 7.16 (m, 1H); 5.28 (s, 2H).

(e) Preparation 5-(4-(3-Bromo-4-(3-fluorobenzyloxy)-anilino)-quinazolin-6-yl)-furan-2-carbaldehyde The title compound was prepared according to Procedure B followed by Procedure C from 6-iodo-(4-(3-fluorobenzyloxy)-3-bromophenyl)-quinazolin-4-yl)amine (1.0 g, 1.82 mmol) and (1,3 dioxolan-2-yl)-2-(tributylstannyl)furan (1.17 g, 2.73 mmol). $^1$H NMR (DMSO-d6) δ 11.89 (bs, 1H); 9.66 (s, 1H); 9.41 (s, 1H); 8.90 (s, 1H); 8.49 (d, 1H); 8.05 (m, 1H); 7.96 (d, 1H); 7.75 (m, 1H); 7.70 (m, 1H); 7.61 (m, 1H); 7.43 (m, 1H); 7.30 (m, 3H); 7.16 (m, 1H); 5.29 (s, 2H).

(f) Preparation of (4-(3-Fluoro-benzyloxy-3-bromophenyl)-(6-(5-((2-methanesulphonyl-ethylamino)-methyl)-furan-2-yl)-quinazolin-4-yl)-amine dihydrochloride The title compound was prepared according to Procedure D from a mixture of 5-(4-(3-Bromo-4-(3-fluorobenzyloxy)-anilino)-quinazolin-6-yl)-furan-2-carbaldehyde (0.623 g, 1.2 mmol) in dichloroethane (12 mL), triethylamine (0.167 mL, 1.2 mmol), acetic acid (0.216 mL 3.6 mmol), and 2-methanesulphonylethylamine (0.447 g, 3.6 mmol). The reaction mixture was warmed to reflux for 1 hour and then cooled to rt before adding sodium triacetoxyborohydride (0.5 g). After 0.5 hours of stirring, another aliquot of sodium triacetoxyborohydride (0.5 g) was added and the reaction was stirred an additional 0.5 hours. The reaction was quenched by the addition of a saturated solution of sodium bicarbonate (aq, 50 mL). EtOAc (50 mL) was added and the layers were separated. The organics were washed with brine and dried over sodium sulfate. The volatiles were removed in vacuo. Purification of the compound was achieved using Biotage column chromatography; eluents: CH2Cl2, EtOH, Et3N (150:8:1). The appropriate fractions were combined and the volatiles were removed in vacuo. The compound was crystallized from EtOAc and Et$_2$O to afford a yellow solid. The hydrochloride salt was made by dissolving the material in a minimal amount of EtOAc and adding 2M HCl in diethyl ether (0.5 mL) to afford a dark yellow solid (0.27 g, 35% yield). $^1$H NMR (DMSO-d6) δ 11.70 (bs, 1H); 9.84 (bs, 2H); 9.59 (s, 1H); 8.89 (s, 1H); 8.39 (d, 1H); 8.14 (s, 1H); 7.93 (d, 1H); 7.80 (d, 1H); 7.45 (m, 1H); 7.31 (m, 4H); 7.16 (m, 1H); 6.83 (m, 1H); 5.30 (s, 2H); 4.43 (s, 2H); 3.67 (m, 2H); 3.40 (m, 2H); 3.12 (s, 3H).

(g) Preparation of (4(3-Fluoro-benzyloxy)-3-bromophenyl)-(6-(5-((2-methanesulphonyl-ethylamino)-methyl)-furan-2-yl)quinazolin-4-yl)-amine ditosylate.

The HCl salt of 5-(4-[3-bromo-4-(3-fluorobenzyloxy)-anilino]-6-quinazolinyl)-furan-2-carbaldehyde, is prepared according to Procedure D and Example 1(e), and is converted to the tosylate salt according to the procedure of Example 1(h). The resultant carbaldehyde tosylate product is used to prepare the (4-(3-Fluoro-benzyloxy)-3-bromophenyl)-(6-(5-((2-methanesulphonyl-ethylamino)-methyl)-furan-2-yl)quinazolin-4-yl)-amine ditosylate according to the procedure of Example 1(i).

Example 3

Preparation of (4-(3-Fluoro-benzyloxy)-3-chlorophenyl)-(6-(2-((2-methanesulphonyl-ethylamino)-methyl)-thiazol-4-yl)quinazolin-4-yl)-amine and di-hydrochloride and ditosylate salts thereof

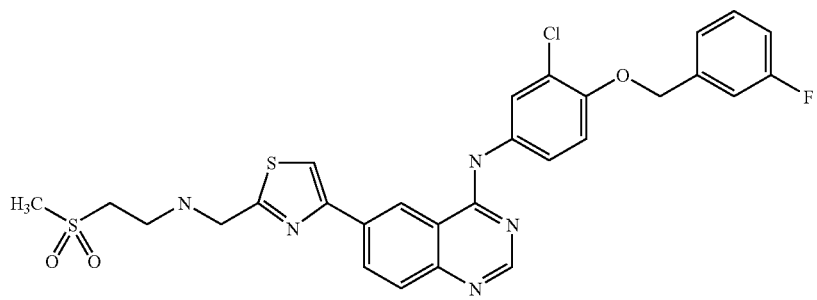

(a) Preparation of N-(4-(3-fluorobenzyloxy)-chlorophenyl)-6-(1-ethoxyvinylether)-quinazolin-4-yl)-amine To a suspension of the 6-iodo-(4-(3-fluorobenzyloxy)-3-chlorophenyl)-quinazolin-4-yl amine (12.6 g, 24.93 mmol) in acetonitrile (100 mL) was added tributyl(1-ethoxyvinyl) stannane (9 g, 24.93 mmol) and bis(triphenylphosphine) palladium (II) chloride (1.75 g, 2.29 mmol). The reaction mixture was refluxed for 18 hours, then filtered through a plug of silica gel. The resulting solution was poured into 5% aqueous NH$_4$OH (200 mL) and extracted with ethyl acetate (500 mL). The organic layer was dried over anhydrous sodium sulfate, concentrated, and purified by silica gel chromatography to provide the title compound as a yellow solid (7.2 g, 64% yield). $^1$H NMR (400 MHz, d$_6$ DMSO) δ 9.92 (s, 1H), 8.76 (s, 1H), 8.58 (s, 1H), 8.08 (m, 1H), 8.01 (m, 1H), 7.76 (m, 2H), 7.48 (m, 1H), 7.32 (m, 3H), 7.22 (m, 1H), 5.28 (s, 2H), 5.02 (s, 1H), 4.56 (s, 1H), 4.01 (q, 2H), 1.42 (t, 3H); ESI-MS m/z 449.9 (M+H)$^+$.

(b) Preparation of N-{4-[(3-fluorobenzyloxy)]-chlorophenyl}-6-[2-({[2-(methanesulphonyl)ethyl]-[trifluoroacetyl]amino}methyl)-1,3-thiazol-4-yl]-quinazolin-4-yl)-amine To a solution of N-(4-(3-fluorobenzyloxy)-chlorophenyl)-6-(1-ethoxyvinylether)-quinazolin-4-yl)-amine (7.1 g, 15.8 mmol) in a THF (150 mL)/H$_2$O (5 mL) mixture cooled to 0° C. was added N-bromosuccinimide (2.81 g, 15.8 mmol). The resulting mixture was stirred for 0.25 hours, then dried over anhydrous sodium sulfate and concentrated. The crude N-(4-(3-fluorobenzyloxy)-chlorophenyl)-6-(bromomethylketone)-quinazolin-4-yl)-amine and N-(trifluoroacetyl)-N-(methanesulphonylethyl)-aminomethylthioamide (4.61 g, 15.8 mmol) were dissolved in DMF (50 mL) and heated at 70° C. for 1 hour. The reaction mixture was concentrated, then diluted with dichloromethane (300 mL) and washed with saturated sodium bicarbonate solution (100 mL). The organic layer was dried over anhydrous sodium sulfate, concentrated, and purified by silica gel chromatography to provide the title compound as a foam (4.6 g, 42% yield). ESI-MS m/z 694.1 (M+H)$^+$.

(c) Preparation of N-{4-[(3-fluorobenzyloxy)]-chlorophenyl}-6-[2-({[2-(methanesulphonyl)ethyl]-amino}methyl)-1,3-thiazol-4-yl]-quinazolin-4-yl)-amine hydrochloride To a solution of N-{4-[(3-fluorobenzyloxy)]-chlorophenyl}-6-[2-({[2-(methanesulphonyl)ethyl]-[trifluoroacetyl]amino}methyl)-1,3-thiazol-4-yl]-quinazolin-4-yl)-amine (4.6 g, 6.63 mmol) in methanol (100 mL) was added 2M NaOH (50 mL). The resulting mixture was stirred at room temperature for 2 hours, concentrated to ½ volume, poured into H$_2$O (100 mL), and extracted with dichloromethane (300 mL). The organic layer was dried over anhydrous sodium sulfate, concentrated, and purified by silica gel chromatography. The resulting amine was dissolved in dichloromethane/methanol (3:1, 100 mL) and then 4M HCl/dioxane (20 mL) was added. The resulting mixture was concentrated and filtered to provide the title compound as a yellow solid (4.0 g, 90% yield). $^1$H NMR (400 MHz, d$_4$ MeOH) δ 9.38 (s, 1H), 8.82 (s, 1H), 8.78 (d, 1H), 8.36 (s, 1H), 7.94 (s, 1H), 7.92 (d, 1H), 7.63 (m, 1H), 7.41 (m, 1H), 7.26 (m, 1H), 7.22 (m, 2H), 7.04 (m, 1H), 5.24 (s, 2H), 4.82 (s, 2H), 3.84 (m, 2H), 3.76 (m, 2H), 3.12 (s, 3H); ESI-MS m/z 597.1 (M+H)$^+$.

(d) Preparation of (4-(3-Fluoro-benzyloxy)-3-chlorophenyl)-(6-(2-((2-methanesulphonyl-ethylamino)-methyl)-thiazol-4-yl)quinazolin-4-yl)-amine ditosylate.

The HCL salt of (4-(3-Fluoro-benzyloxy)-3-chlorophenyl)-(6-(2-((2-methanesulphonyl-ethylamino)-methyl)-thiazol-4-yl)quinazolin-4-yl)-amine was prepared according to Procedures 3(a) to (c) and then converted to the (4-(3-Fluoro-benzyloxy)-3-chlorophenyl)-(6-(2-((2-methanesulphonyl-ethylamino)-methyl)-thiazol-4-yl)quinazolin-4-yl)-amine ditosylate salt according to the procedure of Examples 1 and 2. $^1$H NMR (300 MHz, d6-DMSO) 11.4 (br s, 1H), 9.51 (br s, 1H), 9.24 (s, 1H), 8.95 (s, 1H), 8.68 (d, J=9 Hz, 1H), 8.42 (s, 1H), 7.96 (d, J=9 Hz, 1H), 7.89 (d, J=2 Hz, 1H), 7.64 (dd, J=2, 9 Hz, 1H), 7.47 (m, 5H), 7.34 (m, 3H), 7.20 (t, J=9 Hz, 1H), 7.10 (d, J=8 Hz, 4H), 5.32 (s, 2H), 4.76 (d, 2H), 3.61 (s, 4H), 3.15 (s, 3H), 2.28 (s, 6H).

Biological Data

Tumor Studies: HN5

HN5 cells were cultured in RPMI 1640+10% Fetal bovine serum, Sodium pyruvate and L-Glutamine at 370° in a 95/5% air/CO$_2$ atmosphere. Cells were harvested following trypsin digestion and brought to a density of 2×10$^6$ cells/200 µl in PBS. Tumors were initiated by injection of the cell suspension subcutaneously in the axillary region.

Tumor Studies: BT474

The BT474 xenograft was maintained by serial transplantation in SCID mice. Tumors are initiated by injection of tumor fragments subcutaneously in the axillary region.

Tumor Studies: NCl H322

NCl H322 cells were cultured in RPMI 1640+10% Fetal bovine serum, Sodium pyruvate and L-Glutamine at 37° in a 95/5% air/CO$_2$ atmosphere. Cells were harvested following trypsin digestion and brought to a density of 2×10$^6$ cells/200 µl in PBS. Tumors were initiated by injection of the cell suspension subcutaneously in the axillary region. In addition some experiments were performed following serial transplantation of tumor fragments in SCID mice. Tumors were initiated by injection of tumor fragments subcutaneously in the axillary region.

Tumor Studies: Measurements

For the xenograft models used here solid tumors were measured by electronic caliper measurement through the skin, measurements were typically made twice weekly. In the examples presented, tumors were monitored beyond the duration of therapy Tumor Studies: Formulation and Administration Drugs were administered by P.O. or I.V. routes. The title compound or salt thereof of Example 1 was formulated in aqueous 0.5% hydroxypropyl methylcellulose, 0.1% Tween 80 and administered as a suspension twice daily for 21 days as indicated in the respective figures. Taxol® (Bristol Myers Squibb Co.) was purchased preformulated in Cremophor-EL saline and diluted into saline to a final Cremophor-EL concentration of 5 or 10% Cremophor-EL for 10 or 20 mg/kg Taxol therapy respectively. Taxol was administered I.V., once a day, for 5 days (days 1–5 of Example 1 therapy) as indicated in the respective figures. Carboplatin (Sigma) was formulated in saline and was administered I.V., once a day, for two 5 day periods as indicated in the respective figure (days 1–5 and 15–19 of Example 1 therapy). These studies were performed under IACUC # 468. The results are illustrated in FIGS. 1–3.

Figure 2:
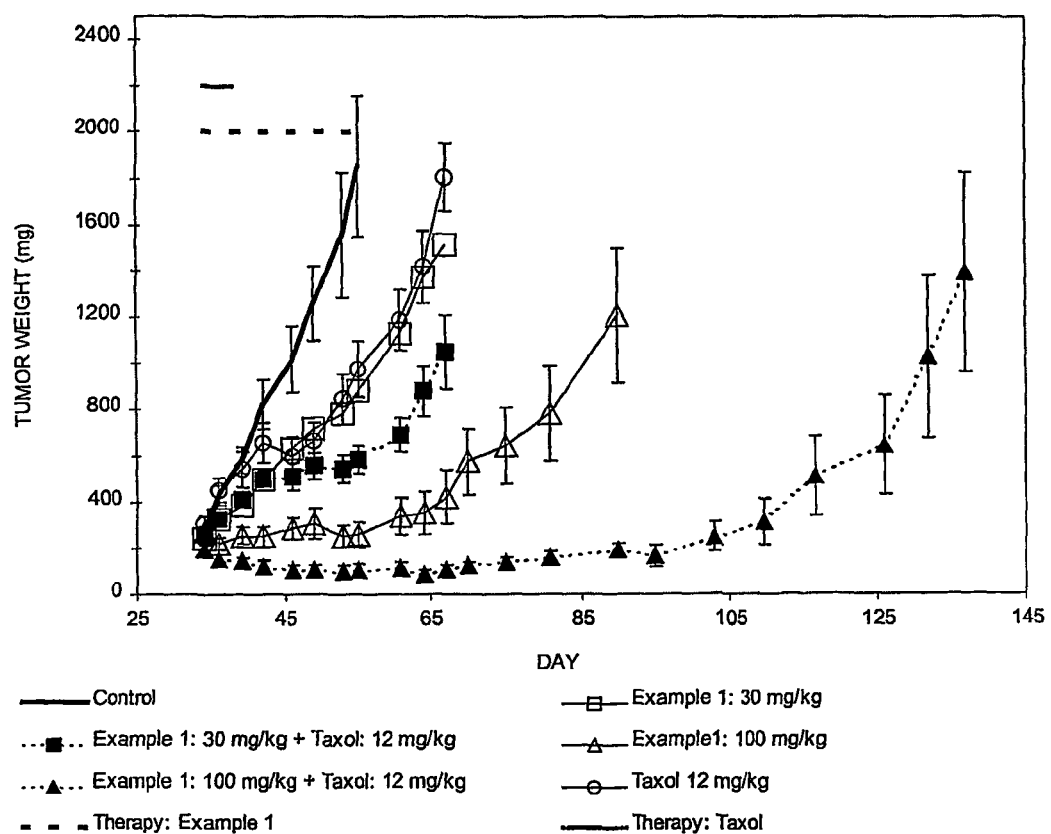
FIG. 2 depicts anti-tumor activity in a subcutaneous human xenograft mouse model dosed with a compound of Example 1 and paclitaxel (Taxol®) individually and in combination versus BT474 (human breast tumor line).

FIG. 1 illustrates dosing of a HN5 (head and neck) subcutaneous human xenograft mouse model with the compound of Example 1 and/or carboplatin. Carboplatin as a montherapy in the HN5 s.c. human xenograft mouse model showed some anti-tumor activity (about 45% tumor growth inhibition at highest dose). Dosing of the compound of Example 1 also showed anti-tumor activity in the same model as monotherapy (about 80% tumor growth inhibition at highest dose). When the compound of Example 1 and carboplatin were used in combination, 100–120% tumor growth inhibition was observed during treatment FIG. 2 illustrates dosing of a BT474 (breast) sub cutaneous human xenograft mouse model with the compound of Example 1 and/or Taxol®. Taxol® dosed as monotherapy in the BT474 s.c. human xenograft mouse model showed some anti-tumor activity (about 45% tumor growth inhibition). The compound of Example 1 also showed anti-tumor activity in the same model when dosed as monotherapy (about 90% tumor growth inhibition at the highest dose tested). When the compound of Example 1 and Taxol® were used in combination, 100–120% anti-tumor activity was observed during treatment. There was a significant delay in tumor re-growth observed, tumor growth inhibition was sustained for approximately 40 days after treatment ceased.

Figure 3:
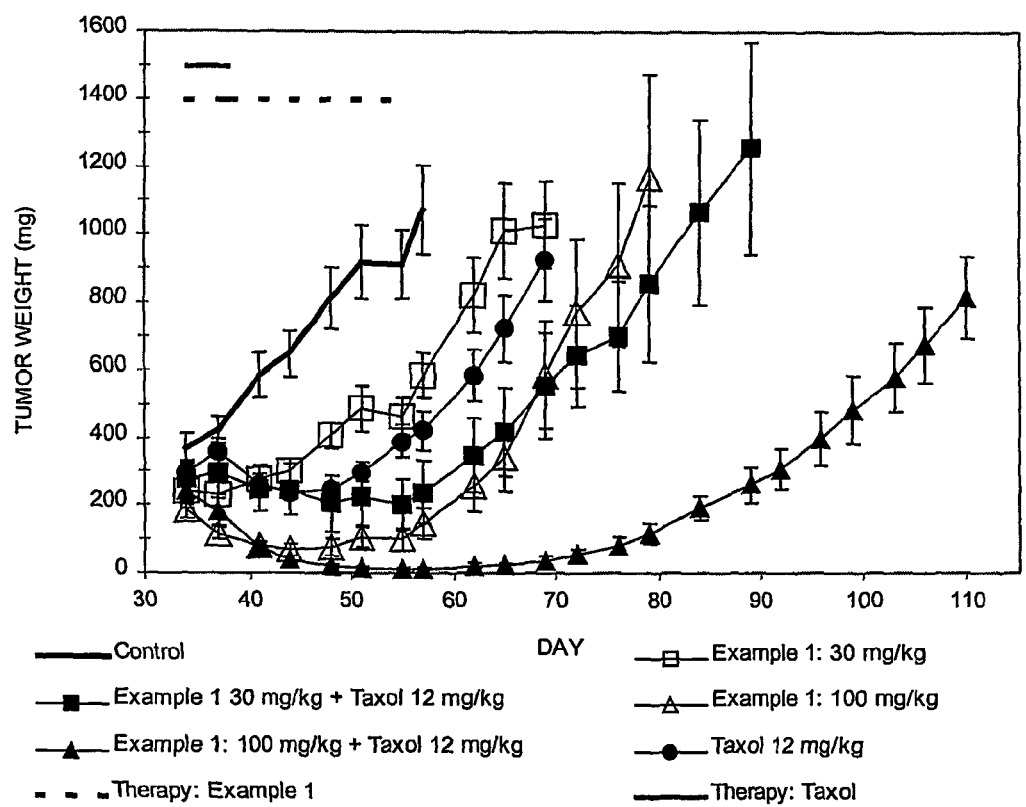
FIG. 3 depicts anti-tumor activity in a subcutaneous human xenograft mouse model dosed with a compound of Example 1 and paclitaxel individually and in combination versus NCl H-322(human lung tumor line).

FIG. 3 illustrates dosing of a NCl H322 (lung) sub cutaneous human xenograft mouse model with the compound of Example 1 and/or Taxol®. Taxol® dosed as monotherapy in the NCl H322 s.c. human xenograft mouse model showed some anti-tumor activity (about 45% tumor growth inhibition). The compound of Example 1 also showed anti-tumor activity in the same model when dosed as monotherapy (about 100–130% tumor growth inhibition). When the compound of Example 1 and Taxol® were used in combination, tumor growth was completely arrested (below detection—not measurable). There was a significant delay in tumor re-growth observed after treatment ceased.

We claim:

1. A method of treating breast cancer in a mammal, comprising: administering to said mammal a therapeutically effective amount of:

(a) a compound of formula II:

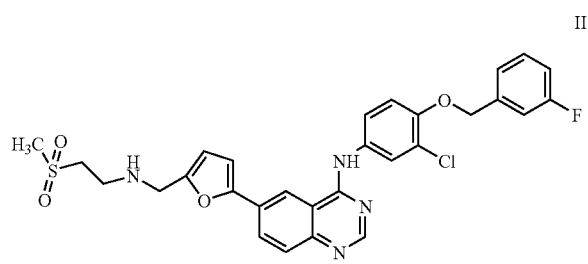

salts, or solvates; and
(b) paclitaxel.

2. The method of claim 1, wherein said method comprises administering to said mammal a therapeutically effective amount of (a) a compound of formula II,

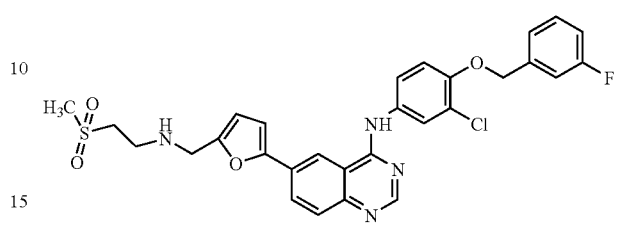

or salt thereof; and
(b) paclitaxel.

* * * * *

UNITED STATES PATENT AND TRADEMARK OFFICE
CERTIFICATE OF CORRECTION

| | |
|---|---|
| PATENT NO. | : 7,141,576 B2 |
| APPLICATION NO. | : 10/466290 |
| DATED | : November 28, 2006 |
| INVENTOR(S) | : Lakey et al. |

It is certified that error appears in the above-identified patent and that said Letters Patent is hereby corrected as shown below:

On the title page, item [75] Inventors should read:

Karen Elizabeth Lackey, Durham, NC, Neil Spector, Chapel Hill, NC; Edgar Raymond Wood, III., Durham, NC, Wenle Xia, Durham, NC; Robert J. Mullin, Durham, NC Signed and Sealed this Twenty-second Day of May, 2007

JON W. DUDAS
*Director of the United States Patent and Trademark Office*